(12) United States Patent
Zhang et al.

(10) Patent No.: US 10,799,245 B2
(45) Date of Patent: Oct. 13, 2020

(54) ABSORBABLE OCCLUDER

(71) Applicant: Lifetech Scientific (Shenzhen) Co., Ltd., Shenzhen (CN)

(72) Inventors: Deyuan Zhang, Shenzhen (CN); Dong Xiang, Shenzhen (CN); Xianmiao Chen, Shenzhen (CN)

(73) Assignee: Lifetech Scientific (Shenzhen) Co. Ltd., Shenzhen (CN)

( * ) Notice: Subject to any disclaimer, the term of this patent is extended or adjusted under 35 U.S.C. 154(b) by 299 days.

(21) Appl. No.: 15/741,679

(22) PCT Filed: Jun. 7, 2016

(86) PCT No.: PCT/CN2016/085020
§ 371 (c)(1),
(2) Date: Jan. 3, 2018

(87) PCT Pub. No.: WO2017/041554
PCT Pub. Date: Mar. 16, 2017

(65) Prior Publication Data
US 2018/0214159 A1 Aug. 2, 2018

(30) Foreign Application Priority Data

Sep. 7, 2015 (CN) .......................... 2015 1 0566831

(51) Int. Cl.
*A61B 17/12* (2006.01)
*A61F 2/02* (2006.01)
(Continued)

(52) U.S. Cl.
CPC ........ *A61B 17/12122* (2013.01); *A61B 17/00* (2013.01); *A61B 17/12031* (2013.01);
(Continued)

(58) Field of Classification Search
CPC ....... A61B 17/12122; A61B 17/12022–12045; A61B 17/12099–12131; A61B 17/12168–12177; A61B 17/0057
See application file for complete search history.

(56) References Cited

U.S. PATENT DOCUMENTS 5,725,552 A * 3/1998 Kotula .................... A61F 2/01
606/213
6,245,103 B1 * 6/2001 Stinson .................... A61F 2/90
623/1.22
(Continued)

FOREIGN PATENT DOCUMENTS

| CN | 101987046 A | 3/2011 |
|---|---|---|
| CN | 103110444 A | 5/2013 |

(Continued)

OTHER PUBLICATIONS

International Search Report dated Sep. 9, 2016 or PCT/CN2016/085020.

*Primary Examiner* — Katrina M Stransky
*Assistant Examiner* — Brigid K Byrd
(74) *Attorney, Agent, or Firm* — Raymond Sun

(57) ABSTRACT

An absorbable occluder (100) comprises a woven mesh (110), wherein the woven mesh (110) comprises at least two polymer filaments with different centralized degradation time periods, or comprises a polymer filament made by blending at least two polymers with different centralized degradation time periods. The absorbable occluder (100) can avoid the tissue inflammatory response caused by the polymer filaments of the woven mesh (110) centralized degrading within the same period.

17 Claims, 6 Drawing Sheets

(51) Int. Cl.
*A61B 17/00* (2006.01)
*A61L 31/06* (2006.01)
*A61L 31/14* (2006.01)
*A61L 31/04* (2006.01)

(52) U.S. Cl.
CPC .. *A61B 17/12109* (2013.01); *A61B 17/12177* (2013.01); *A61F 2/02* (2013.01); *A61L 31/041* (2013.01); *A61L 31/06* (2013.01); *A61L 31/148* (2013.01); *A61B 2017/00004* (2013.01)

(56) References Cited

U.S. PATENT DOCUMENTS

| | | | |
|---|---|---|---|
| 6,319,264 B1 | 11/2001 | Tormala et al. | |
| 6,379,368 B1* | 4/2002 | Corcoran | A61B 17/0057 606/153 |
| 9,173,733 B1* | 11/2015 | Lim | A61F 2/04 |
| 2001/0034531 A1* | 10/2001 | Ho | A61B 17/12022 606/151 |
| 2004/0193206 A1* | 9/2004 | Gerberding | A61B 17/12022 606/200 |
| 2006/0122647 A1* | 6/2006 | Callaghan | A61B 17/0057 606/213 |
| 2011/0082495 A1* | 4/2011 | Ruiz | A61B 17/0057 606/213 |
| 2013/0030455 A1* | 1/2013 | Subramanian | A61B 17/0057 606/157 |
| 2013/0178886 A1* | 7/2013 | Liu | A61B 17/12172 606/198 |
| 2013/0317527 A1* | 11/2013 | Jacinto | A61B 17/0057 606/151 |

FOREIGN PATENT DOCUMENTS

| | | |
|---|---|---|
| CN | 203677142 U | 7/2014 |
| CN | 204181658 U | 3/2015 |
| EP | 1674048 | 6/2006 |

* cited by examiner

ABSORBABLE OCCLUDER

TECHNICAL FIELD

The present disclosure relates to a cardiovascular medical device, and particularly relates to an absorbable occluder which can be used for occluding defects in the heart or blood vessels.

BACKGROUND OF THE DISCLOSURE

Atrial septal defect (ASD), ventricular septal defect (VSD) and patent ductus arteriosus (FDA) are several common congenital heart defects. The interventional therapy of closing the defect with an occluder, with its few trauma, safety, and positive near term and midterm effects, is a preferred therapy method for patients with heart defect indications.

Currently, most occluders are formed of shape memory alloy. After the occluder is implanted into the body, the tissue ingrowth around the defect and the endothelialization of the occluder are completed, and the occluder will exist in the defect area permanently. The occluder made of the metal alloy material has a risk of generating long-term complications such as atrioventricular block, valvular injury, residual shunt, cardiac perforation and metal allergy, etc. Furthermore, the occluder is normally implanted into a child, so the useful life of the occluder is generally expected to be the lifetime of the patient. However, the current clinical history is only 20 years, and the longer-term safety requires further follow-up.

As a new generation of occluders, an absorbable polymer occluder is made of a biodegradable polymer material such as polylactic acid (PLA), polyglycolic acid (PGA), polyhydroxyalkanoate (PHA), polydioxanone (PDO) and polycaprolactone (PCL), etc. The absorbable polymer occluder can degrade to be absorbed by the body after endothelialization to ensure that the defect is completely healed by the patient's own tissues, so that the long-term complications caused by the permanent retention of the metal alloy occluder in the body are eliminated. The absorbable polymer occluder mainly comprises a woven mesh and a flow-resistant film sutured into the woven mesh. Currently, the woven mesh is generally formed of a polymer material, and can relatively rapidly degrade as a whole within a certain time period in the degradation process to release a large number of residual products from the degraded polymer, known as degradation products, of which exceeds the volume that can be absorbed by the body's tissues, thereby potentially leading to serious inflammatory response.

SUMMARY OF THE DISCLOSURE

The present disclosure is to provide an absorbable polymer occluder to solve a technical problem, wherein serious inflammatory response caused by intensive release of polymer degradation products within centralized degradation time periods is avoided.

A first technical scheme adopted by the present disclosure is as follows: an absorbable occluder comprises a woven mesh, and the woven mesh comprises at least two polymer filaments, and the at least two polymer filaments have different centralized degradation time periods.

A second technical scheme adopted by the present disclosure is as follows: an absorbable occluder comprises a woven mesh, and the woven mesh comprises a polymer filament comprising at least two polymers with different centralized degradation time periods. For example, at least part of one polymer filament can be made of a blend of the at least two polymers with different centralized degradation time periods; or part of one polymer filament is made of one of the at least two polymers, and the other part is made of the other polymer in the at least two polymers, namely different parts of one polymer filament are formed by polymers with different centralized degradation time periods.

For any preceding technical scheme, in one of the embodiments, the woven mesh comprises 20-200 polymer filaments.

For any preceding technical scheme, in one of the embodiments, the polymer filaments are made of a material selected from polylactic acid (PLA), polyglycolic acid (PGA), polylactic-co-glycolic acid (PLGA), polyhydroxyalkanoate (PHA), polydioxanone (PDO), polycaprolactone (PCL), polyimide, polyanhydride, polyphosphoester, polyurethane or polycarbonate, or a copolymer of at least two of the polymer monomers.

For any preceding technical scheme, in one of the embodiments, the filament diameters of the polymer filaments range from 0.05 mm to 0.50 mm.

For any preceding technical scheme, in one of the embodiments, the weight average molecular weights of the material of the polymer filaments range from 20,000 Da to 800,000 Da.

For any preceding technical scheme, in one of the embodiments, the polydispersity coefficient of the material of the polymer filaments is 1.2-5.

For any preceding technical scheme, in one of the embodiments, the crystallinity of the material of the polymer filaments ranges from 0% to 80%.

For any preceding technical scheme, in one of the embodiments, the occluder further comprises a flow-resistant film which is sewn in the woven mesh through a suture.

For any preceding technical scheme, in one of the embodiments, the flow-resistant film is made of a material selected from polyethylene terephthalate (PET), polyethylene (PE), polylactic acid (PLA), polyglycolic acid (PGA), polylactic-co-glycolic acid (PLGA), polyhydroxyalkanoate (PHA), polydioxanone (PDO), polycaprolactone (PCL), polyamide, polyanhydride, polyphosphoester, polyurethane or polycarbonate, or a copolymer of at least two of the polymer monomers.

For any preceding technical scheme, in one of the embodiments, the suture is made of a material selected from polylactic acid (PLA), polyglycolic acid (PGA), polylactic-co-glycolic acid (PLGA), polyhydroxyalkanoate (PHA), polydioxanone (PDO), polycaprolactone (PCL), polyamide, polyanhydride, polyphosphoester, polyurethane or polycarbonate, or a copolymer of at least two of the polymer monomers.

For any preceding technical scheme, in one of the embodiments, the occluder further comprises a locking mechanism of which one end is provided with a through hole and an internal thread and the other end is of a cylinder structure without through holes. One end of the locking mechanism is connected to a distal end, and the other end of the locking mechanism is detachably connected to a proximal end, and the distance between double disks, namely the waist height, of the occluder is fixed when the other end of the locking mechanism is matched with the proximal end.

For any preceding technical scheme, in one of the embodiments, the locking mechanism is made of a material selected from at least one of polylactic acid (FLA), polyglycolic acid (PGA), polylactic-co-glycolic acid (PLGA), polyhydroxyalkanoate (PHA), polydioxanone (PDO), polycaprolactone (PCL), polyamide, polyanhydride, polyphosphoester, polyurethane or polycarbonate, or a copolymer of at least two of the polymer monomers.

Compared with the prior art, regarding the occluders made of the polymer filaments with the same mass, the polymer filaments of the woven mesh disclosed herein include a polymer filament made of a blend of the at least two polymers with different centralized degradation time periods, or include the at least two polymer filaments with different centralized degradation time periods. The different polymers disclosed herein are subjected to centralized degradation within different time periods, so that the phenomenon of the centralized degradation within a certain time period of the occluder worked in-vivo of the prior art, which would result in serious tissue inflammatory response, is now avoided.

DETAILED DESCRIPTION

In order to understand the technical features, objectives and effects of the present disclosure more explicitly, the detailed description of the present disclosure will be now explained in detail by reference to the accompanying drawings. However, the protective scope of the present disclosure is not limited to this respect.

In the interventional medical field, a distal end is defined as the end far away from the operator during a surgical procedure, and a proximal end is defined as the end close to the operator during a surgical procedure.

If classified by the shape, the occluder generally includes two structures of an approximately I-shaped structure and an approximately T-shaped structure. The I-shaped structure can be understood to have double disks and a waist mechanism, and have the structure of a small waist and a large disk. If classified by the applied heart defect area, the occluder mainly includes a ventricular septal defect (VSD) occluder, an atrial septal defect (ASD) occluder, a patent ductus arteriosus (FDA) occlude, and a patent foramen ovale (PFO) occluder, wherein the VSD occluder, the ASD occluder and the PFO occluder are of an approximately I-shaped structure provided with double disks and a waist mechanism, and the PDA occluder is of an approximately T-shaped structure provided with a single disk and a waist mechanism.

The structure and material of the occluder provided by the present disclosure is described in detail by taking an I-shaped double-disk occluder as an example below, however, the occluder provided by the present disclosure is not limited to this structure.

Figure 1:
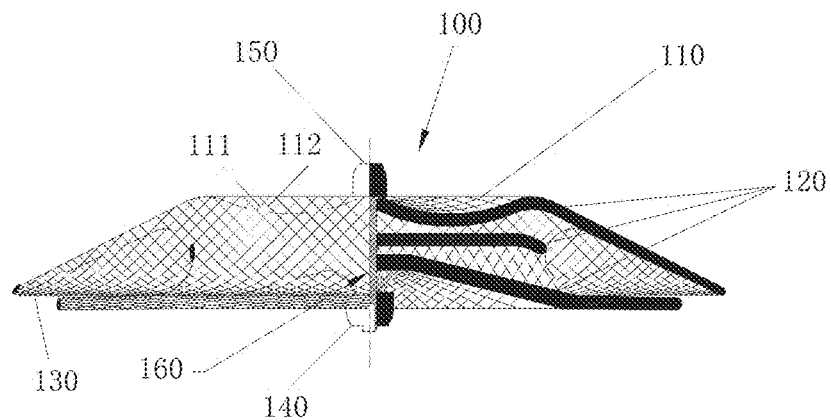
FIG. 1 is a schematic structural diagram of an occluder made according to one embodiment of the present disclosure.
Figure 2:
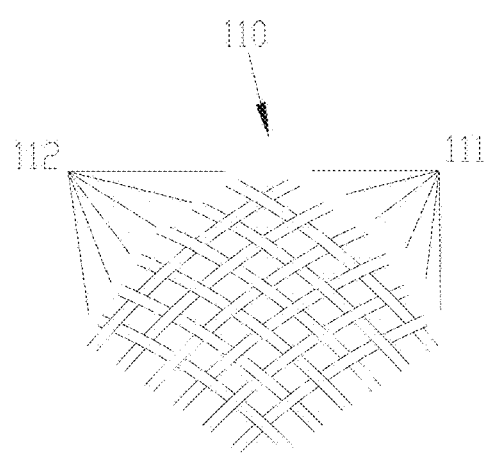
FIG. 2 is a main view of a mesh tube of an occluder made according to one embodiment of the present disclosure.
Figure 3:
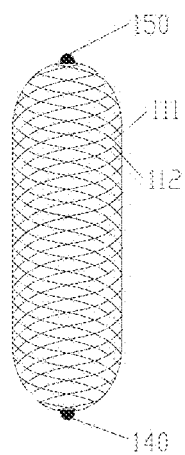
FIG. 3 is a schematic weaving diagram of a woven mesh of an occluder according to embodiment 1 of the present disclosure.

As shown in FIG. 1, a double-disk occluder 100 provided by an embodiment of the present disclosure comprises a woven mesh 110, a flow-resistant film 120 disposed in the woven mesh 110 and sutured in the woven mesh 110, and a locking mechanism 160. As shown in FIG. 2, a plurality of polymer filaments are divided into a first weaving group 111 and a second weaving group 112. The plurality of polymer filaments in the first weaving group 111 and the plurality of polymer filaments in the second weaving group 112 are arranged in parallel to one another, and the two weaving groups are automatically and alternately woven into well-shaped grids on a cylinder to form a tubular structure. All the polymer filaments at the proximal end of the tubular structure are tightened into a sleeve and are molten and welded into a bolt head 140, and all the polymer filaments at the distal end are tightened and fixed in the sleeve and are molten and welded into a sealing head 150, so that a mesh tube as shown in FIG. 3 is obtained. The mesh tube structure is subjected to a tooling for thermal treatment and then is cooled to obtain the double-disk woven mesh 110; and the flow-resistant film 120 made of degradable polymers is sutured in the woven mesh 110 by using a suture 130 made of degradable polymers. In other words, the woven mesh 110 comprises a plurality of a first weaving group 111 and a second weaving group 112 which are made of polymer materials. One end of the locking mechanism 160 is connected to the sealing head 150, the other end of the locking mechanism 160 is detachably connected to the bolt head 140, and when the other end of the locking mechanism 160 is matched with the bolt head 140, the distance between double disks, namely the waist height, of the occluder 110 is fixed, and the double-disk structure of the occluder 110 is set. The locking mechanism 160 can be made of a biodegradable polymer material such as at least one selected from polylactic acid (FLA), polyglycolic acid (PGA), polylactic-co-glycolic acid (PLGA), polyhydroxyalkanoate (PHA), polydioxanone (PDO), polycaprolactone (PCL), polyamide, polyanhydride, polyphosphoester, polyurethane or polycarbonate, or a copolymer of at least two of the polymer monomers. The structure of the locking mechanism 160 and the connection method of the woven mesh 110 are not limited to this respect, and the universal structure and connection methods that are known in the relevant art can be adopted as long as the waist height of the occluder can be locked to a predetermined value (namely the to-be-occluded defect depth), which will not be described in detail here.

In definition of the polymer degradation process of the present disclosure, the ratio of the residual mass to the initial mass of the polymers is the mass retention rate of the polymers. When the mass retention rate is reduced to 5% and below, the polymers are completely degraded. If the mass retention rate of the polymers is reduced relatively rapidly within a certain period of time, the polymers are defined to be subjected to centralized degradation within the period of time. When the mass retention rate of the polymers in the present disclosure is reduced to 5% and below every two months, the polymers are regarded to be subjected to centralized degradation within the two months; and if the mass retention rate is lower than 5%, the polymers are defined to be slowly degraded. The total centralized degradation time period of the polymers is defined as a centralized degradation time period of the polymers, and the mass reduced in a polymer degradation process is regarded as the release amount of degradation products.

In order to study the degradation period, the centralized degradation time of different polymer filaments, the release condition of the degradation products as well as the mechanical properties of the polymer filaments degraded for 6 months according to the present invention, the different polymer filaments are soaked into a 37° C. phosphate buffering solution so as to be subjected to an in-vitro degradation experiment.

After the in-vitro degradation experiment for the polymer filaments has been performed for 6 months, the mechanical properties of the degradable polymer filaments are tested by using a universal tester to obtain the elastic modulus and elongation at break of the polymer filaments, and the test standard and condition are respectively GB/T228-2010, setting the initial distance 10 mm and the stretching speed 1 mm/min. If the polymer filaments still have a certain elastic modulus (not lower than 1 GPa) and elongation at break (not lower than 20%) after being degraded for 6 months, the occluder made of the polymer filaments can be judged to still maintain a stable frame structure after 6 months.

The polymer filaments subjected to the in-vitro degradation experiment is sampled and weighed every two months to obtain a test result with the precision of 1/1,000,000 g, and thus a relation curve between mass reduction of the polymer filaments and time is obtained, namely, a trend curve that the mass retention rate is changed over time. The centralized degradation time interval of the polymers is the centralized degradation time period of the polymers.

In order to study the influences of the products released from the occluder degradation to the inflammatory foreign body reaction, degradable occluders made in different embodiments are implanted into the hearts of pigs, and the pigs subjected to animal experiments are followed-up and observed. The pigs are euthanized after two years implantation. The occluders and myocardial tissues surrounding the occluders are taken out and subjected to pathological section analysis to obtain the pathological image of the occluders and myocardial tissues surrounding the occluders.

Embodiment 1

Figure 4:
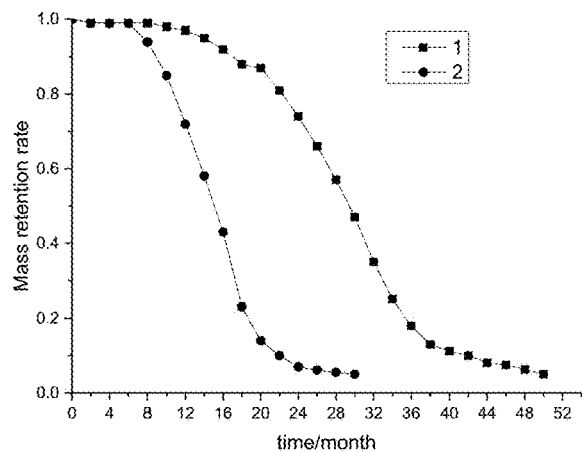
FIG. 4 is a trend diagram of in-vitro degradation of two polymer filaments of embodiment 1 under a 37° C. condition.
Figure 5:
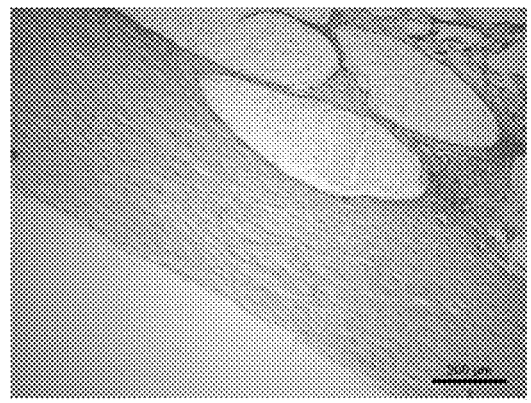
FIG. 5 is a pathological image of an occluder and myocardial tissues surrounding the occluder of embodiment 1 after 2 years of implantation into a pig heart.

This embodiment provides an occluder having the overall mass of a woven mesh being 0.726 g. A first weaving group comprises 36 mutually-arranged poly(L-lactic acid) (PLLA) filaments with the diameters of 0.50 mm and 36 mutually-parallel-arranged PLLA filaments with the diameters of 0.15 mm, wherein the PLLA filaments in the first weaving group have the molecular weight of 100,000 Da, the molecular weight distribution coefficient of 1.50 and the crystallinity of 48%; the PLLA filaments in the second weaving group have the molecular weight of 100,000 Da, the molecular weight distribution coefficient of 1.49 and the crystallinity of 49%. The two filaments are subjected to an in-vitro degradation experiment and are measured to respectively have the elastic modulus of 3.89 GPa and 3.08 GPa as well as the elongations at break of 72% and 63% after being degraded for 6 months, which prove that the occluder made of the two polymer filaments in the embodiment can maintain a stable frame structure within 6 months' implantation and can realize complete endothelial coverage: and the trends of the mass retention rates of the two filaments along with time extension are respectively as shown in curves 1 and 2 in FIG. 4. The PLLA filaments with the filament diameters of 0.50 mm have the complete degradation time, namely the degradation period, of 4-5 years and the centralized degradation time period from the 20th month to the 38th month, and the PLLA filaments with the filament diameters of 0.15 mm have the degradation period of 2-3 years and the centralized degradation time period from the 6th month to the 20th month. The two filaments are subjected to centralized degradation within completely different time periods, so that the release of a large amount of degradation products within the same time period can be avoided; and the occluder and myocardial tissues surrounding the occluder are subjected to pathological section analysis after the occluder in the embodiment has been implanted into the heart of a pig for 2 years; the pathological image of the occluder and myocardial tissues surrounding the occluder is as shown in FIG. 5, and no obvious inflammation and foreign body reactions are found.

Embodiment 2

Figure 6:
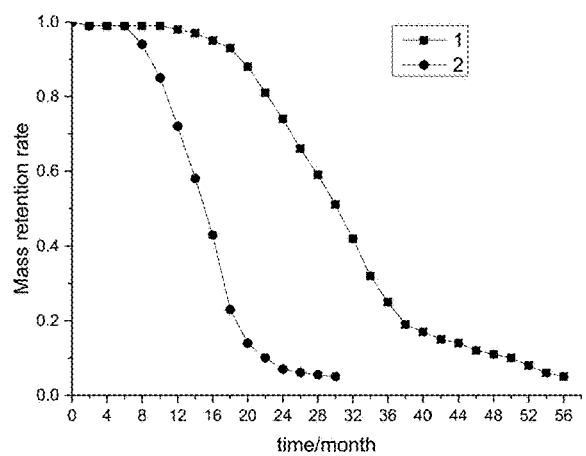
FIG. 6 is a trend diagram of in-vitro degradation of two polymer filaments of embodiment 2 under a 37° C. condition.
Figure 7:
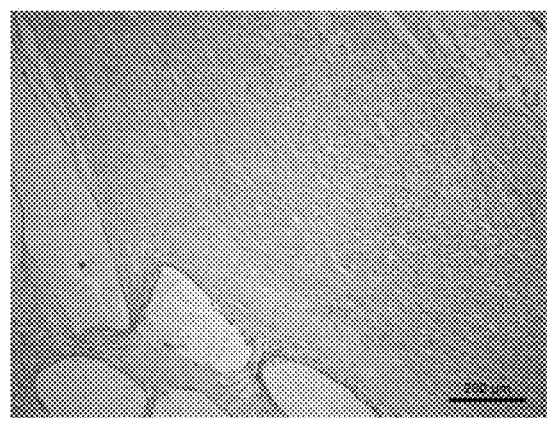
FIG. 7 is a pathological image of an occluder and myocardial tissues surrounding the occluder of embodiment 2 after 2 years of implantation into a pig heart.

In an occluder provided by the embodiment, a first weaving group comprises 48 polyhydroxyalkanoate (PHA) filaments with the molecular weight of 800,000 Da, and a second weaving group comprises 48 polycaprolactone (PCL) filaments with the molecular weight of 100,000 Da. The PHA filaments of the first weaving group have the molecular weight distribution coefficient of 4.80, the filament diameter of 0.05 mm and the crystallinity of 30%; and the PLC filaments of the second weaving group have the molecular weight distribution coefficient of 1.90, the filament diameter of 0.15 mm and the crystallinity of 50%. The two filaments are subjected to an in-vitro degradation experiment and are measured to respectively have the elastic modulus of 4.39 GPa and 3.28 GPa as well as the elongations at break of 84% and 65% after being degraded for 6 months, which prove that the occluder made of the two polymer filaments in the embodiment has a stable frame structure within 6 months' implantation and can realize complete endothelial coverage; and the trends of the mass retention rates of the two filaments along with time extension are respectively as shown in curves 1 and 2 in FIG. 6. The PHA filaments have the degradation period of 4-5 years and the centralized degradation time period from the 18th month to the 38th month, and the PCL filaments have the degradation period of 2-3 years and the centralized degradation time period from the 6th month to the 20th month, and the two filaments are subjected to centralized degradation within different time periods, so that the release of a large amount of degradation products within the same time period can be avoided. The occluder and myocardial tissues surrounding the occluder are subjected to pathological section analysis after the occluder in the embodiment has been implanted into the heart of a pig for 2 years. The pathological image of the occluder and myocardial tissues surrounding the occluder is as shown in FIG. 7, and no obvious inflammation and foreign body reactions are found.

Embodiment 3

Figure 8:
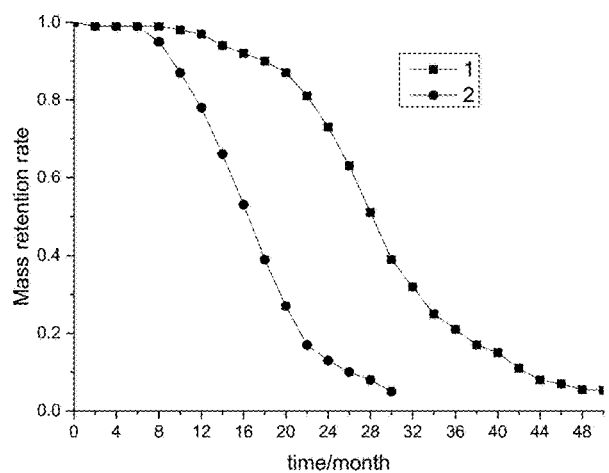
FIG. 8 is a trend diagram of in-vitro degradation of two polymer filaments of embodiment 3 under a 37° C. condition.
Figure 9:
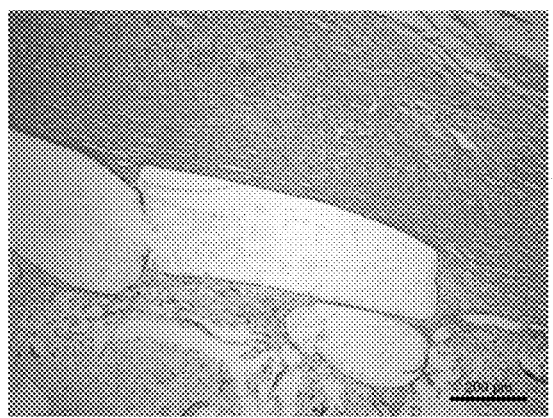
FIG. 9 is a pathological image of an occluder and myocardial tissues surrounding the occluder of embodiment 3 after 2 years of implantation into a pig heart.

In an occluder provided by the embodiment, a first weaving group comprises 10 PLLA filaments with the crystallinity of 80%, and a second weaving group comprises 10 PLGA filaments with the crystallinity of 20%. Each of the first weaving group and the second weaving group has the filament diameter of 0.25 mm, the molecular weight of 200,000 Da and the molecular weight distribution coefficient of 1.69. The two filaments are subjected to an in-vitro degradation experiment and are measured to respectively have the elastic modulus of 3.56 GPa and 2.65 GPa as well as the elongations at break of 76% and 60% after being degraded for 6 months, which prove that the occluder made of the two polymer filaments in the embodiment has a stable frame structure within 6 months' implantation and can realize complete endothelial coverage; and the trends of the mass retention rates of the two filaments along with time extension are respectively as shown in curves 1 and 2 in FIG. 8, and the PLLA filaments have the complete degradation time of 4-5 years and the centralized degradation time period from the 20th month to the 34th month. The PLGA filaments have the complete degradation time of 2-3 years and the centralized degradation time period from the 8th month to the 22nd month, and the two filaments are subjected to centralized degradation within different time periods, so that the release of a large amount of degradation products within the same time period can be avoided. The occluder and myocardial tissues surrounding the occluder are subjected to pathological section analysis after the occluder in the embodiment has been implanted into the heart of a pig for 2 years, the pathological image of the occluder and myocardial tissues surrounding the occluder is as shown in FIG. 9, and no obvious inflammation and foreign body reactions are found.

Embodiment 4

Figure 10:
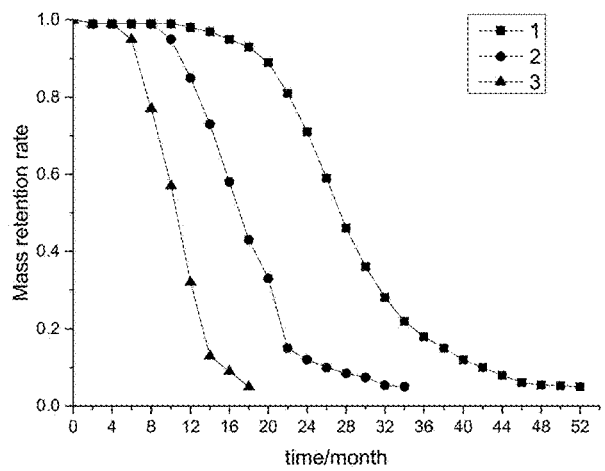
FIG. 10 is a trend diagram of in-vitro degradation of three polymer monofilaments of embodiment 4 under a 37° C. condition.
Figure 11:
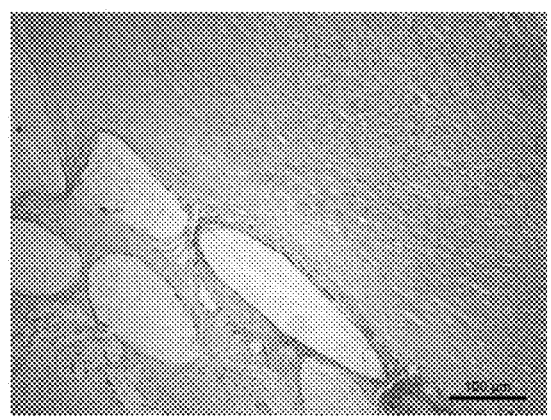
FIG. 11 is a pathological image of an occluder and myocardial tissues surrounding the occluder of embodiment 4 after 2 years of implantation into a pig heart.

In an occluder provided by the embodiment, a first weaving group comprises 96 poly(L-lactic acid) (PLLA) filaments, and a second weaving group comprises 48 poly-DL-lactic acid (PDLLA) filaments and 48 polylactic-co-glycolic acid (PLGA) filaments. The PLLA filaments have the molecular weight of 300,000 Da, the molecular weight distribution coefficient of 1.60, the filament diameter of 0.15 mm and the crystallinity of 50%. The PDLLA is an amorphous polymer and has the molecular weight of 200,000 Da, the molecular weight distribution coefficient of 1.80 and the filament diameter of 0.15 mm, and PLGA is an amorphous polymer and has the molecular weight of 20,000 Da, the molecular weight distribution coefficient of 1.80 and the filament diameter of 0.15 mm. The three filaments are subjected to an in-vitro degradation experiment and are measured to respectively have the elastic modulus of 4.20 GPa, 3.14 GPa and 1.16 GPa as well as the elongations at break of 80%, 55% and 39% after being degraded for 6 months, which prove that the occluder made of the three polymer filaments in the embodiment has a stable frame structure within 6 months' implantation and can realize complete endothelial coverage; and the trends of the mass retention rates of the three filaments along with time extension are respectively as shown in curves 1, 2 and 3 in FIG. 10. The PLLA filaments have the complete degradation time of 4-5 years and the centralized degradation time period from the 18th month to the 36th month, and the PDLLA filaments have the complete degradation period of 2-3 years and the centralized degradation time period from the 10th month to the 22nd month. The PLGA filaments have the complete degradation time of 1-2 years and the centralized degradation time period from the 6th month to the $14^{th}$ month. The three filaments are subjected to centralized degradation within different time periods, so that the release of a large amount of degradation products within the same time period can be avoided. The occluder and myocardial tissues surrounding the occluder are subjected to pathological section analysis after the occluder in the embodiment has been implanted into the heart of a pig for 2 years, the pathological image of the occluder and myocardial tissues surrounding the occluder is as shown in FIG. 11, and no obvious inflammation and foreign body reactions are found.

Embodiment 5

Figure 12:
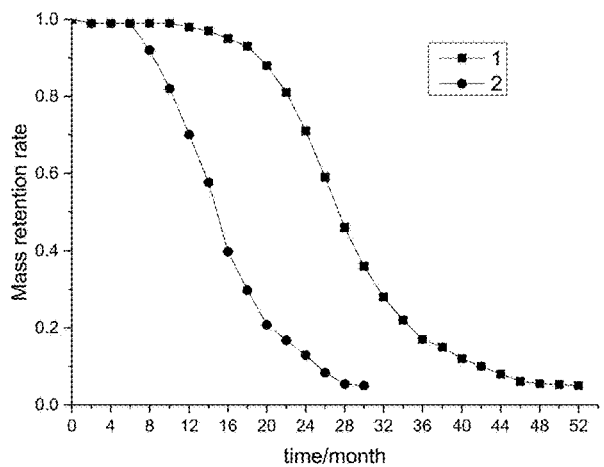
FIG. 12 is a trend diagram of in-vitro degradation of two polymer filaments of embodiment 5 under a 37° C. condition.
Figure 13:
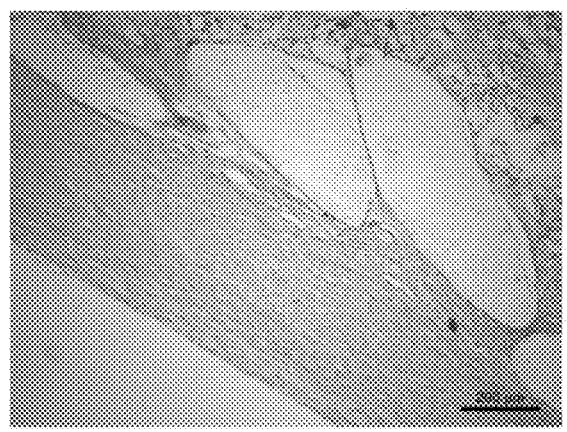
FIG. 13 is a pathological image of an occluder and myocardial tissues surrounding the occluder of embodiment 5 after 2 years of implantation into a pig heart.

In an occluder provided by the embodiment, a first weaving group comprises 48 PLLA filaments of which the surfaces are subjected to hydrophilic treatment, and a second weaving group comprises 56 PLLA filaments of which the surfaces are not treated. The PLLA filaments in each of the two weaving groups have the molecular weight of 300,000 Da, the molecular weight distribution coefficient of 1.60, the filament diameter of 0.15 mm and the crystallinity of 50%, wherein the PLLA filaments of which the surfaces are subjected to hydrophilic treatment are more easily degraded after being in contact with water, while the degradation rate of the PLLA filaments of which the surfaces are not subjected to hydrophilic treatment is relatively low. The two filaments are subjected to an in-vitro degradation experiment and are measured to respectively have the elastic modulus of 4.20 GPa and 2.97 GPa as well as the elongations at break of 80% and 58% after being degraded for 6 months, which prove that the occluder made of the two polymer filaments in the embodiment has a stable frame structure within 6 months after being implanted and can realize complete endothelial coverage; and the trends of the mass retention rates of the two filaments along with time extension are respectively as shown in curves 1 and 2 in FIG. 12. The polymer filaments of which the surfaces are not subjected to hydrophilic treatment have the degradation time of 4-5 years and the centralized degradation time period from the 18th month to the 36th month, and the polymer filaments of which the surfaces are subjected to hydrophilic treatment have the degradation period of 2-3 years and the centralized degradation time period from the 6th month to the 20th month. The two filaments are subjected to centralized degradation within different time periods, so that the release of a large amount of degradation products within the same time period in a service process of the occluder can be avoided. The occluder and myocardial tissues surrounding the occluder are subjected to pathological section analysis after the occluder in the embodiment has been implanted into the heart of a pig for 2 years, the pathological image of the occluder and myocardial tissues surrounding the occluder is as shown in FIG. 13, and no obvious inflammation and foreign body reactions are found.

Embodiment 6

Figure 14:
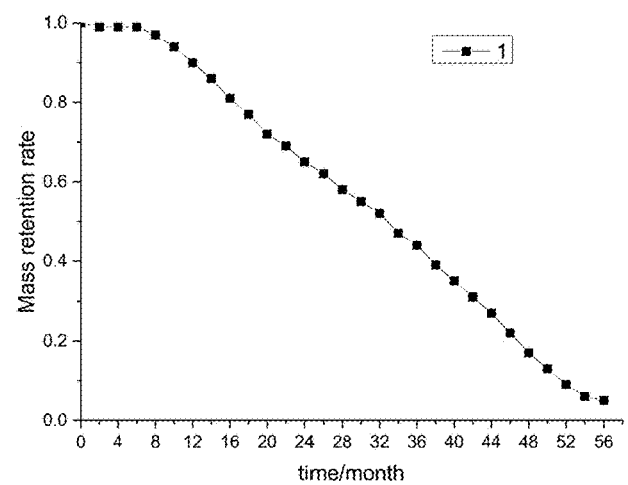
FIG. 14 is a trend diagram of in-vitro degradation of blended polymer filaments of embodiment 6 under a 37° C. condition.
Figure 15:
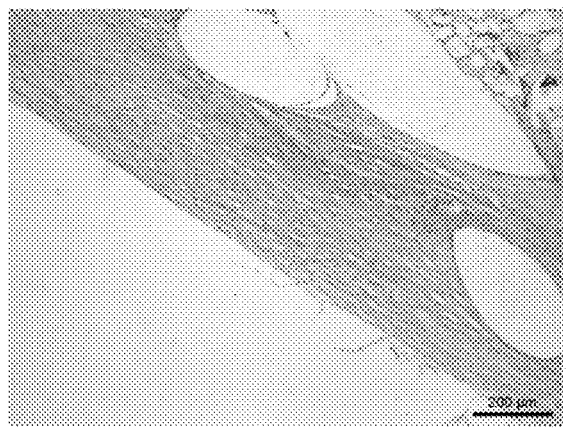
FIG. 15 is a pathological image of an occluder and myocardial tissues surrounding the occluder of embodiment 6 after 2 years of implantation into a pig heart.

An occluder provided by the embodiment comprises 92 woven filaments made by wiredrawing after melting and blending PLLA particles and PLGA particles according to the mass ratio of 1:1, and the filament diameters of the woven filaments are 0.15 mm, wherein the selected PLLA particles have the weight average molecular weight of 500,000 Da, the molecular weight distribution coefficient of 1.60 and the crystallinity of 50%. The selected amorphous polymer PLGA particles have the weight average molecular weight of 200,000 Da and the molecular weight distribution coefficient of 2.70. The mixed filaments are measured to have the elastic modulus of 3.21 GPa and the elongations at break of 67% after being degraded for 6 months, which prove that the occluder made of the mixed filaments in the embodiment has a stable frame structure within 6 months after being implanted and can realize complete endothelial coverage; and the trend of the mass retention rate of the mixed filaments along with time extension is as shown in FIG. 14. The degradation time of the polymer filaments of the mixed filaments is 4-5 years, and the mixed filaments are gently degraded from the 8th month to the 52nd month within a degradation period, so that the release of a large amount of degradation products within the same time period in a service process of the occluder can be avoided. The occluder and myocardial tissues surrounding the occluder are subjected to pathological section analysis after the occluder in the embodiment has been implanted into the heart of a pig for 2 years, the pathological image of the occluder and myocardial tissues surrounding the occluder is as shown in FIG. 15, and no obvious inflammation and foreign body reactions are found.

Comparative Example 1

Figure 16:
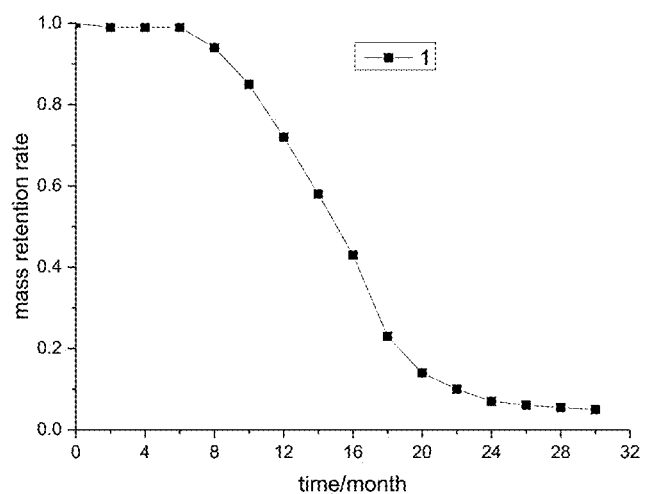
FIG. 16 is a trend diagram of in-vitro degradation of a single polymer filament in a comparative example 1 under a 37° C. condition.
Figure 17:
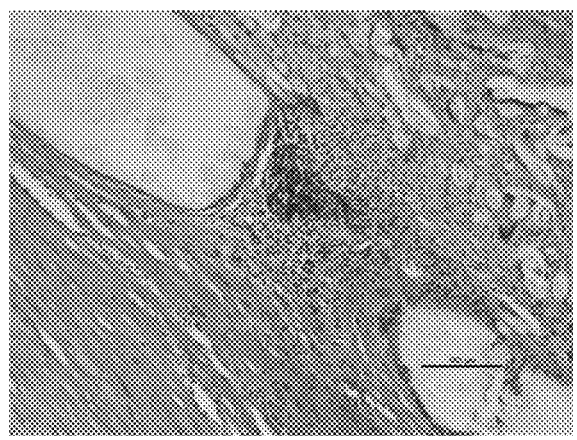
FIG. 17 is a pathological image of an occluder and myocardial tissues surrounding the occluder in a comparative example 1 after 2 years of implantation into a pig heart.

In an occluder provided by the comparative example, the overall mass of a woven mesh of the occluder is 0.726 g, and the woven mesh comprises 96 PLLA filaments with the diameter of 0.15 mm, wherein 48 of the PLLA filaments are arranged in parallel to one another to form a first weaving group, and the other 48 PLLA filaments are arranged in parallel to one another to form a second weaving group. The PLLA filaments have the molecular weight of 100,000 Da, the molecular weight distribution coefficient of 1.49 and the crystallinity of 49%. The PLLA filaments are subjected to an in-vitro degradation experiment and are measured to have the elastic modulus of 3.08 GPa and the elongations at break of 63% after being degraded for 6 months, which prove that the occluder made in the comparative example has a stable frame structure within 6 months after being implanted and can realize complete endothelial coverage: and the trend of the mass retention rate of the polymer filaments along with time extension is as shown in FIG. 16. The degradation period of the polymer filaments is 2-3 years, the polymer filaments are subjected to centralized degradation from the 6th month to the 20th month, and a large amount of degradation products are released within the time period. The occluder and myocardial tissues surrounding the occluder are subjected to pathological section analysis after the occluder in the comparative example has been implanted into the heart of a pig for 2 years, the pathological image of the occluder and myocardial tissues surrounding the occluder is as shown in FIG. 17, and inflammation and foreign body reactions are relatively serious after the occluder has been implanted for 2 years.

Experimental results of the embodiments 1 and 6 and the comparative example 1 show that the woven mesh of the occluder is woven by using a polymer filament made by blending at least two polymers with different centralized degradation time periods or at least two polymer filaments with different centralized degradation time periods, on the basis that the occluder is kept to have the stable frame structure in an early stage (6 months) of implantation, the polymers making the polymer filaments release degradation products within different centralized degradation time periods, and thus avoiding serious inflammatory response caused by the release of a large amount of the degradation products within the same time period in the service process of the occluder.

The invention claimed is:

1. An absorbable occluder comprising a woven mesh, wherein said woven mesh comprises at least two polymer filaments, and said at least two polymer filaments have different centralized degradation time periods; wherein the occluder further comprises a proximal disk, a distal disk, a waist between the proximal and distal disks, a locking mechanism connecting the proximal and distal disks in a fixed position and having a first end and a second end, and with the waist having a waist height, wherein the second end of said locking mechanism is connected to a distal end of the occluder, the first end of said locking mechanism is detachably connected to a proximal end of the occluder, and the waist height is fixed when the first end of the locking mechanism is matched with the proximal end; and wherein when a mass retention rate of the at least two polymer filaments is reduced to 5% and below every two months, the at least two polymer filaments are regarded to be subjected to centralized degradation within the two months, and wherein the total centralized degradation time period of the at least two polymer filaments is defined as a centralized degradation time period of the at least two polymer filaments.

2. The absorbable occluder of claim 1, wherein said woven mesh comprises 20-200 polymer filaments.

3. The absorbable occluder of claim 1, wherein said polymer filaments are made of a material selected from polylactic acid, polyglycolic acid, polylactic-co-glycolic acid, polyhydroxyalkanoate, polydioxanone, polycaprolactone, polyamide, polyanhydride, polyphosphoester, polyurethane or polycarbonate, or a copolymer of at least two of the polymer monomers.

4. The absorbable occluder of claim 1, wherein the filament diameters of said polymer filaments range from 0.05 mm to 0.50 mm.

5. The absorbable occluder of claim 1, wherein the weight average molecular weights of said polymer filaments range from 20,000 Da to 800,000 Da.

6. The absorbable occluder of claim 1, wherein the polydispersity coefficients of said polymer filaments are 1.2-5.

7. The absorbable occluder of claim 1, wherein the crystallinity of said polymer filaments ranges from 0% to 80%.

8. The absorbable occluder of claim 1, wherein said occluder further comprises a flow-resistant film, and wherein said flow-resistant film is fixed in the woven mesh through a suture, and said flow-resistant film is made of a material selected from polyethylene terephthalate, polyethylene, polylactic acid, polyglycolic acid, polylactic-co-glycolic acid, polyhydroxyalkanoate, polydioxanone, polycaprolactone, polyamide, polyanhydride, polyphosphoester, polyurethane or polycarbonate, or a copolymer of at least two of the polymer monomers, and said suture is made of a material selected from polylactic acid, polyglycolic acid, polylactic-co-glycolic acid, polyhydroxyalkanoate, polydioxanone, polycaprolactone, polyamide, polyanhydride, polyphosphoester, polyurethane or polycarbonate, or a copolymer of at least two of the polymer monomers.

9. The absorbable occluder of claim 1, wherein the second end of the locking mechanism is connected to a sealing head, and the first end of the locking mechanism is detachably connected to a bolt head.

10. An absorbable occluder comprising a woven mesh, wherein said woven mesh comprises a polymer filament, and the polymer filament comprises at least two polymers with different centralized degradation time periods; wherein the occluder further comprises a proximal disk, a distal disk, a waist between the proximal and distal disks, a locking mechanism connecting the proximal and distal disks in a fixed position and having a first end and a second end, and with the waist having a waist height, wherein the second end of said locking mechanism is connected to a distal end of the occluder, the first end of said locking mechanism is detachably connected to a proximal end of the occluder, and the waist height is fixed when the first end of the locking mechanism is matched with the proximal end; and wherein when a mass retention rate of the polymer filament is reduced to 5% and below every two months, the polymer filament is regarded to be subjected to centralized degradation within the two months, and wherein the total centralized degradation time period of the polymer filament is defined as a centralized degradation time period of the polymer filament.

11. The absorbable occluder of claim 10, wherein said polymer filament is made of a material selected from polylactic acid, polyglycolic acid, polylactic-co-glycolic acid, polyhydroxyalkanoate, polydioxanone, polycaprolactone, polyamide, polyanhydride, polyphosphoester, polyurethane or polycarbonate, or a copolymer of at least two of the polymer monomers.

12. The absorbable occluder of claim 10, wherein the filament diameter of said polymer filament ranges from 0.05 mm to 0.50 mm.

13. The absorbable occluder of claim 10, wherein the weight average molecular weight of said polymer filament ranges from 20,000 Da to 800,000 Da.

14. The absorbable occluder of claim 10, wherein the polydispersity coefficient of said polymer filament is 1.2-5.

15. The absorbable occluder of claim 10, wherein the crystallinity of said polymer filament is from 0% to 80%.

16. The absorbable occluder of claim 10, wherein said occluder further comprises a flow-resistant film, and wherein said flow-resistant film is fixed in the woven mesh through a suture, and said flow-resistant film is made of a material selected from polyethylene terephthalate, polyethylene, polylactic acid, polyglycolic acid, polylactic-co-glycolic acid, polyhydroxyalkanoate, polydioxanone, polycaprolactone, polyamide, polyanhydride, polyphosphoester, polyurethane or polycarbonate, or a copolymer of at least two of the polymer monomers, and said suture is made of a material selected from polylactic acid, polyglycolic acid, polylactic-co-glycolic acid, polyhydroxyalkanoate, polydioxanone, polycaprolactone, polyamide, polyanhydride, polyphosphoester, polyurethane or polycarbonate, or a copolymer of at least two of the polymer monomers.

17. The absorbable occluder of claim 10, wherein the second end of the locking mechanism is connected to a sealing head, and the first end of the locking mechanism is detachably connected to a bolt head.

\* \* \* \* \*